(12) United States Patent
Wilson

(10) Patent No.: US 7,871,443 B2
(45) Date of Patent: Jan. 18, 2011

(54) PROSTHETIC FOOT WITH COMPOSITE HEEL

(76) Inventor: Michael T. Wilson, 2711 Cartwright Rd., Missouri City, TX (US) 77459

( * ) Notice: Subject to any disclaimer, the term of this patent is extended or adjusted under 35 U.S.C. 154(b) by 738 days.

(21) Appl. No.: 11/364,113

(22) Filed: Feb. 28, 2006

(65) Prior Publication Data

US 2007/0203585 A1 Aug. 30, 2007

(51) Int. Cl.
*A61F 2/68* (2006.01)
(52) U.S. Cl. .......................... 623/53; 623/49
(58) Field of Classification Search .................. 623/49, 623/53
See application file for complete search history.

(56) References Cited

U.S. PATENT DOCUMENTS

| | | | |
|---|---|---|---|
| 409,311 A | 8/1889 | Snyder | |
| 419,019 A | 1/1890 | Kolbe | |
| 766,686 A | 8/1904 | Gault | |
| 1,071,230 A | 8/1913 | Hanger | |
| 1,155,545 A | * 10/1915 | Bracht | ......................... 403/156 |
| 1,294,632 A | 2/1919 | Dickson | |
| 2,450,728 A | 10/1948 | Havens | |
| 2,594,752 A | 4/1952 | Fahlstrom | |
| 2,605,475 A | 8/1952 | Burger et al. | |
| 2,620,485 A | 12/1952 | Greissinger | |
| 2,731,645 A | 1/1956 | Woodall | |
| 2,745,108 A | 5/1956 | Withers | |
| 3,196,463 A | 7/1965 | Farneth | |
| 3,480,972 A | 12/1969 | Prahl | |
| 3,940,804 A | 3/1976 | Benton et al. | |
| 3,945,737 A | 3/1976 | Herbenar | |
| 3,982,278 A | 9/1976 | May | |
| 4,134,159 A | 1/1979 | Wilson | |
| 4,328,594 A | 5/1982 | Campbell et al. | |
| 4,387,472 A | 6/1983 | Wilson | |

(Continued)

FOREIGN PATENT DOCUMENTS

AT    0196553    3/1958

(Continued)

OTHER PUBLICATIONS

Flex-Foot, Inc flyers entitled, "Something Revolutionary is in the Air", "adjust the foot, not the lifestyle", "Engineered for the Long Run", Simply Precise, engineered Flexibility, Designed for a Growing Market, Amputee Profile, (Mary J. Gardner), "Amputee Profile (D Broome)", and Flex-Foot, Inc., Newsletter, Issue No. 4, 1992; (16 p ).

(Continued)

*Primary Examiner*—Bruce E Snow
*Assistant Examiner*—Melissa Hoban
(74) *Attorney, Agent, or Firm*—Conley Rose, P.C.

(57) ABSTRACT

Apparatus and methods for a keel for use in a prosthetic foot. In an embodiment, the keel comprises a forefoot portion having a toe end, wherein the forefoot portion comprises a first material. In addition, the keel comprises a mid-foot portion contiguous with the forefoot portion, wherein the mid-foot portion comprises a second material. Further, the keel comprises a heel portion contiguous with the mid-foot portion, wherein the heel portion comprises a third material. Still further, the second material and third material comprise different materials.

7 Claims, 6 Drawing Sheets

U.S. PATENT DOCUMENTS

| | | | |
|---|---|---|---|
| 4,446,580 A | 5/1984 | Furuya et al. | |
| 4,461,045 A | 7/1984 | Shorter et al. | |
| 4,463,459 A | 8/1984 | Shorter et al. | |
| 4,547,913 A | 10/1985 | Phillips | |
| 4,645,509 A | 2/1987 | Poggi et al. | |
| 4,721,510 A | 1/1988 | Cooper et al. | |
| 4,764,172 A | 8/1988 | McCoy | |
| 4,822,363 A | 4/1989 | Phillips | |
| 4,865,612 A * | 9/1989 | Arbogast et al. | 623/55 |
| 4,889,458 A | 12/1989 | Taylor | |
| 4,892,554 A | 1/1990 | Robinson | |
| 4,969,911 A | 11/1990 | Greene | |
| 5,030,239 A | 7/1991 | Copes | |
| 5,037,444 A * | 8/1991 | Phillips | 623/55 |
| 5,112,356 A | 5/1992 | Harris et al. | |
| 5,116,384 A | 5/1992 | Wilson et al. | |
| 5,156,632 A * | 10/1992 | Wellershaus | 623/55 |
| 5,158,570 A | 10/1992 | Schey et al. | |
| 5,219,364 A | 6/1993 | Lloyd | |
| 5,258,038 A | 11/1993 | Robinson et al. | |
| 5,376,140 A | 12/1994 | Ryan | |
| 5,443,527 A | 8/1995 | Wilson | |
| 5,482,513 A * | 1/1996 | Wilson | 623/52 |
| 5,545,234 A | 8/1996 | Collier, Jr. | |
| 5,549,714 A | 8/1996 | Phillips | |
| 5,695,526 A | 12/1997 | Wilson | |
| 5,728,171 A * | 3/1998 | Bryant et al. | 623/38 |
| 5,800,570 A | 9/1998 | Collier | |
| 6,165,177 A | 12/2000 | Wilson et al. | |
| 6,228,124 B1 * | 5/2001 | Slemker et al. | 623/47 |
| 6,231,618 B1 * | 5/2001 | Schall et al. | 623/38 |
| 6,511,514 B1 | 1/2003 | Wilson | |
| 6,572,659 B1 * | 6/2003 | Ryan | 623/55 |
| 6,712,860 B2 * | 3/2004 | Rubie et al. | 623/55 |
| 6,719,807 B2 * | 4/2004 | Harris | 623/55 |
| 2002/0082713 A1 | 6/2002 | Townsend et al. | |
| 2004/0068327 A1 * | 4/2004 | Christensen | 623/52 |
| 2004/0225376 A1 * | 11/2004 | Townsend et al. | 623/52 |
| 2005/0033450 A1 * | 2/2005 | Christensen | 623/52 |
| 2005/0033451 A1 | 2/2005 | Aigner et al. | |
| 2005/0060045 A1 * | 3/2005 | Smith et al. | 623/49 |
| 2005/0071018 A1 * | 3/2005 | Phillips et al. | 623/52 |
| 2005/0085926 A1 * | 4/2005 | Christensen | 623/47 |
| 2007/0250178 A1 * | 10/2007 | Wilson | 623/53 |

FOREIGN PATENT DOCUMENTS

| | | |
|---|---|---|
| DE | 814025 | 9/1951 |
| DE | 2241971 | 3/1974 |
| DE | 9104823 | 6/1991 |
| EP | 224373 | 6/1987 |
| EP | 0280004 | 8/1988 |
| FR | 0481770 | 10/1916 |
| FR | 1233031 | 10/1960 |
| FR | 504342 | 6/1990 |
| FR | 2640499 | 6/1990 |
| GB | 227290 | 1/1925 |
| GB | 621576 | 4/1949 |
| GB | 731223 | 6/1955 |
| GB | 2070439 | 9/1981 |
| GB | 2092451 | 8/1982 |
| SU | 169349 | 11/1951 |
| SU | 1391643 | 4/1988 |
| SU | 1409258 | 7/1988 |
| SU | 1424831 | 9/1988 |
| SU | 1747062 | 7/1992 |
| WO | 8400681 | 3/1984 |
| WO | 8800815 | 2/1988 |
| WO | 8806431 | 9/1988 |

OTHER PUBLICATIONS

Otto Bock Flyer, "1M1—Otto Bock Multiaxial Foot"; (1982) (4 p.).
Campbell-Childs, Inc brochure and flyer (14th anniversary—1979-1993). entitled "The all New ' Sportsman' S A F E II",(12 p).
Devcon instruction sheet # 7041 on "Flexane Urethane"; Jul. 1992; (2 p).
Boston Gear catalog, Self-Aligning Bearings. p. D68; (1 p).
Hosmer brochure; The Quantum Foot; (5 p).
Campbell-Childs, Inc Stationary attachment Flexible Endoskelton II Mailer. Jul. 1989 (2 p).
Campbell-Childs, Inc S A F E Prosthetic Foot Catalog; (8 p.).
United States Manufacturing Company—Multiplex Brochure; "Now More Flexibility for Amputees Who Use the Multiplex"; 1988; (1 p.).
The Ohio Willow Wood Co , "Step into the Future with the Carbon Copy II Energy Storing Foot"; (4 p).
Footnotes (Flex-Foot)—Mailer, Mar. 1989; (4 p).
Flex-Foot, Inc—Price List (Sep. 1, 1989); (8 p).

\* cited by examiner

PROSTHETIC FOOT WITH COMPOSITE HEEL

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

1. Field of the Invention

The present invention relates generally to a prosthetic foot. More particularly, the present invention relates to a prosthetic foot with a composite heel operable to simulate the flexion normally provided by an anatomical ankle.

2. Background of the Invention

A useful prosthesis must simulate the operation and motion of an anatomical foot. In addition, for Syme amputees (e.g., amputees who have sustained an ankle disarticulation), a useful prosthesis must simulate the operation, flexion, and motion of an anatomical ankle.

An anatomical foot, including the ankle joint, is capable of motion around three perpendicular axes, as well as varying degrees of flexure. Specifically, the anatomical foot and ankle are capable of dorsiflexion, planiflexion, inversion, eversion, and transverse rotation. Dorsiflexion and planiflexion comprise the movement of the ball of the foot upward and downward, respectively, with respect to the heel. Inversion and eversion are the twisting of the foot around its longitudinal axis, resulting in outward and inward tilting of the ankles, respectively. Transverse rotation occurs when the foot rotates with respect to the longitudinal axis of the leg, such as occurs during left and right turns of the body.

Some prosthetic feet that include an ankle prosthesis may be capable of complicated motion (e.g., motion around two or three axes). In particular, such prostheses may be useful for Syme amputees since the inclusion of a prosthetic ankle may simulate the operation, flexion, and motion normally provided by an anatomical ankle. However, inclusion of a prosthetic ankle may add bulky moving parts and additional weight to the prosthesis. The additional weight may result in a prosthesis that is too heavy for some patients, such as geriatric patients, very young patients, or other patients who suffer some degree of muscular weakness.

Moreover, although some flexibility may be desirable, a prosthetic foot must also provide a secure and relatively rigid means for coupling the prosthetic foot to the amputee. Some conventional prosthetic feet may provide a rigid metal plate that is bolted to the prosthetic foot to couple the prosthetic foot to the amputee. However, the use of a metal plate may add additional bulk and reduce the flexibility of the prosthetic foot, as well as create stress concentration areas in the prosthetic foot around the bolt attachment points. Concentration of stresses proximal to the areas where the prosthetic foot flexes may lead to premature weakening, cracking, or breaking of the prosthetic foot.

In addition, it is desirable for a prosthetic foot to provide a spring effect during use (e.g., be capable of absorbing, storing, and releasing energy). At a minimum, the prosthesis should store enough energy to return itself to a relaxed, unflexed position when external forces are removed. Such a spring effect may be accomplished by the inclusion of energy storing components such as coil springs. However, such energy-storing components may significantly increase the weight of the prosthesis.

Finally, it is necessary that a prosthetic foot be strong enough to support its wearer and durable enough to withstand the stresses of repeated stepping motions over long periods of time. Some conventional prostheses may be designed for maximize strength, at the cost of added bulk and weight, making them unsuitable for some amputees.

Thus, there remains a need to develop methods and apparatus for improved foot prostheses which overcome some of the foregoing difficulties while providing more advantageous overall results.

BRIEF SUMMARY OF SOME OF THE PREFERRED EMBODIMENTS

These and other needs in the art are addressed in one embodiment by a prosthetic foot keel. In an embodiment, the keel comprises a forefoot portion having a toe end, wherein the forefoot portion comprises a first material. In addition, the keel comprises a mid-foot portion contiguous with the forefoot portion, wherein the mid-foot portion comprises a second material. Further, the keel comprises a heel portion contiguous with the mid-foot portion, wherein the heel portion comprises a third material. Still further, the second material and third material comprise different materials.

These and other needs in the art are addressed in another embodiment by a keel for a prosthetic foot. In an embodiment, the keel comprises a forefoot portion having a toe end. In addition, the keel comprises a mid-foot portion contiguous with the forefoot. Further, the keel comprises a heel portion contiguous with the mid-foot portion. Still further, the keel comprises a semi-spherical dome integral with the mid-foot portion.

These and other needs in the art are addressed in another embodiment by a prosthetic foot. In an embodiment, the prosthetic foot comprises a keel, wherein the keel comprises a forefoot portion, a mid-foot portion, and a heel portion. In addition, the forefoot portion comprises a first material, the mid-foot portion comprises a second material, and the heel portion comprises a third material, wherein the second material and third material are different. Further, the prosthetic foot comprises a means for adjusting the orientation of the keel relative to an amputee about three orthogonal axes and supporting the keel in a desired orientation. Still further, the prosthetic foot comprises a means for simulating the flexion of an anatomical ankle.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more detailed description of the preferred embodiment of the present invention, reference will now be made to the accompanying drawings, wherein.

DETAILED DESCRIPTION OF THE INVENTION

Figure 1:
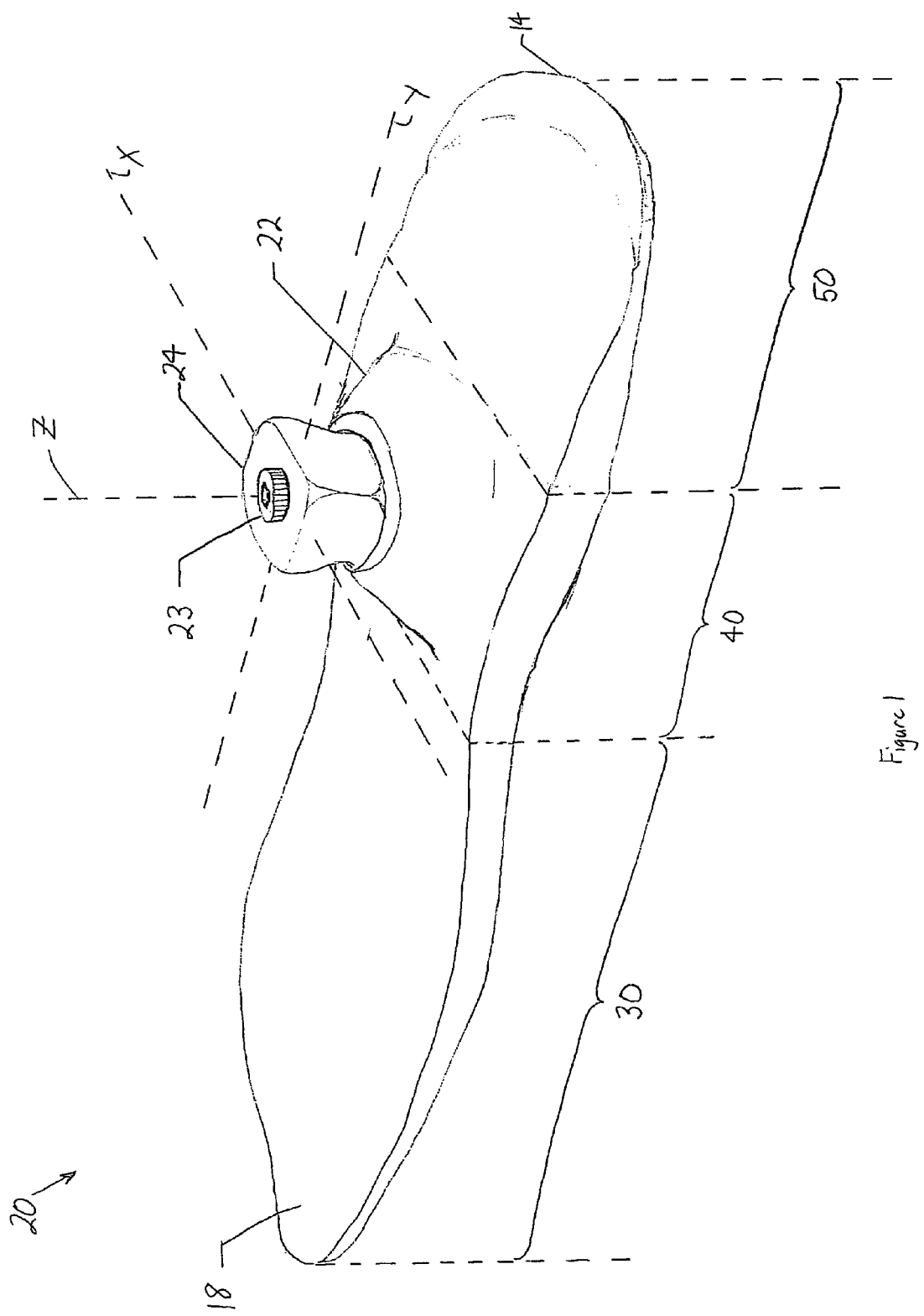
FIG. 1 is a perspective view of an embodiment of a keel of the present invention.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular system components. As one skilled in the art will appreciate, different persons may refer to a component by different names. This document does not intend to distinguish between components that differ in name but not function. The drawing figures are not necessarily to scale. Certain features of the invention may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections.

For purposes of discussion, composites, or composite materials, are materials consisting of more than one constituent material. Some composites are composed of two constituent materials, namely a matrix, which may be continuous and may surround the second phase, and a substrate (e.g., dispersed phase, reinforcing phase). The substrate may be embedded in the matrix. The substrate (e.g., dispersed phase, reinforcing phase) may comprise any suitable material including without limitation, a metal or metal alloy (e.g., aluminum, titanium, stainless steel, etc.), a non-metal (e.g., fiberglass, carbon fiber, kevlar, quartz, polymer, ceramic, etc.) or combinations thereof. In addition, the substrate may comprise more than one constituent material (e.g., a substrate may comprise both carbon fibers and glass fibers). The matrix of a composite may comprise any suitable material including without limitation, a metal or metal alloy (e.g., aluminum, titanium, stainless steel, copper, etc.), a non-metal (e.g., resin, epoxy, polyester, polymer, ceramic, urethane, elastomer, etc.), or combinations thereof.

For purposes of discussion, the x-, y-, and z-axes are shown in FIG. 1 and have been assigned as follows. The x-axis is perpendicular to both the leg and foot, passing through the sides of the ankle. Generally, dorsiflexion and planiflexion (e.g., movement of the ball of the foot upward and downward, respectively) may occur about the x-axis. The y-axis is perpendicular to the leg and parallel to the foot. Generally, inversion and eversion (e.g., the twisting of the foot around its longitudinal axis) may occur about the y-axis. The z-axis is parallel to the leg. Generally, transverse rotation (rotation of the foot with respect to the longitudinal axis of the leg) may occur about the z-axis. It is to be understood that the three axes (x-axis, y-axis, and z-axis) are orthogonal. In addition, in the context of the present discussion, "length" refers to a distance substantially along the y-axis, "width" refers to a distance substantially along the x-axis, and "thickness" refers to a distance substantially along the z-axis.

Figure 2:
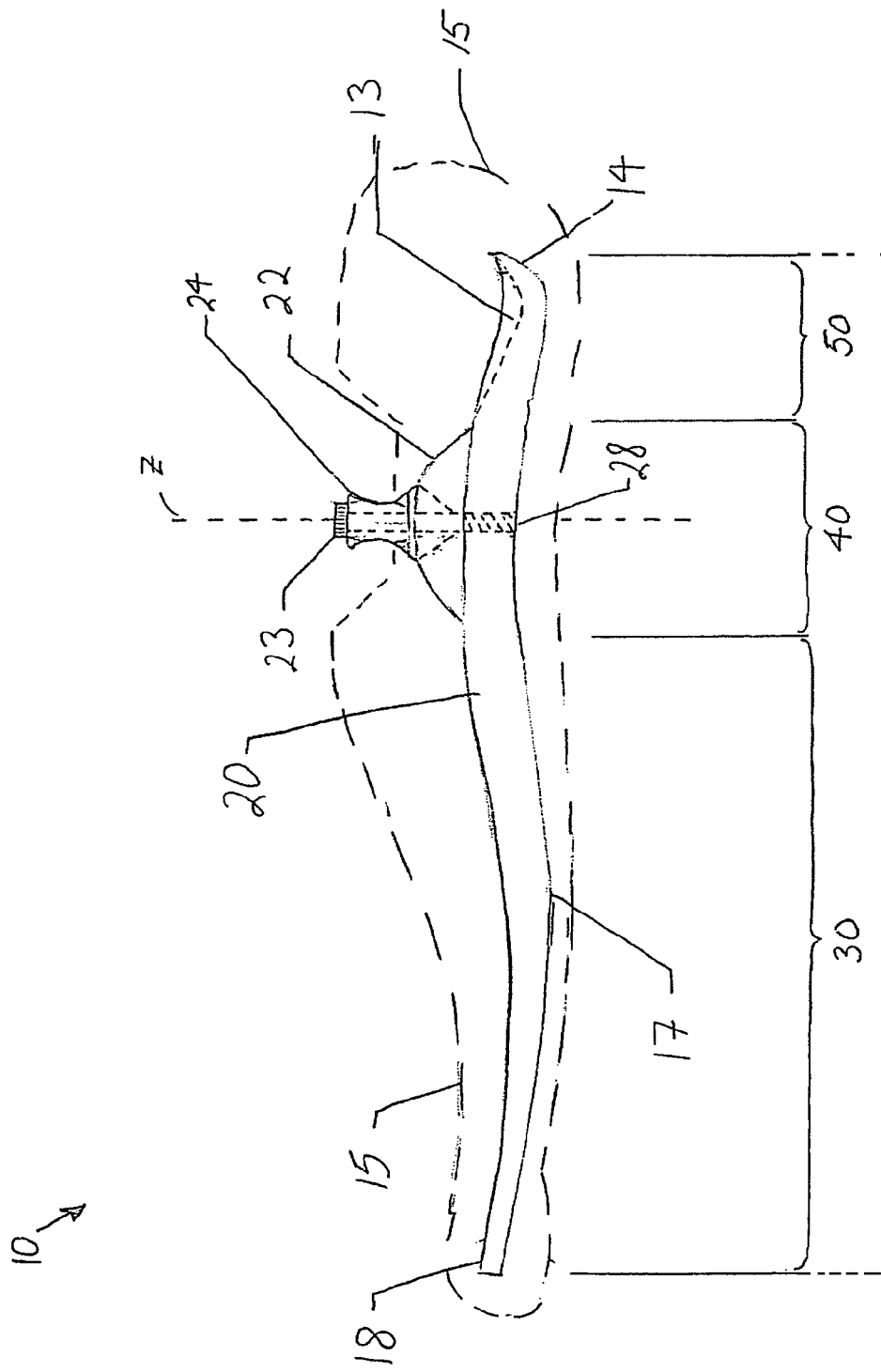
FIG. 2 is a side view of a prosthetic foot including the keel of FIG. 1.

FIGS. 1 and 2 illustrate an embodiment of a prosthetic foot 10 comprising a keel 20 and a cosmesis 15 (shown in phantom in FIG. 2), which together closely replicate the structure and form of an anatomical foot. Keel 20 comprises a forefoot portion 30, a mid-foot portion 40, and a heel portion 50. Forefoot portion 30 includes a toe end 18 and is contiguous with mid-foot portion 40. Mid-foot portion 40 includes a dome 22 and is contiguous with forefoot portion 30 and heel portion 50. In addition, mid-foot portion 40 comprises a vertical borehole 28 extending at least partially therethrough. A connecting spindle 24 is coupled to keel 20 through borehole 28. Heel portion 50 comprises a heel end 14 and a recess 13 (shown in phantom in FIG. 2). The overall length of keel 20 is the sum of the lengths of forefoot portion 30, mid-foot portion 40, and heel portion 50. In preferred embodiments, keel 20 may range in length from 22 to 30 cm.

Forefoot portion 30 further comprises a roll contact 17 along its length. Roll contact 17 may be the general region about which the forefoot of prosthetic foot 10 contacts the ground during a normal forward or backward step. In select embodiments, roll contact 17 may be located between 30% and 50% of the length of keel 20, from toe end 18. Preferably, roll contact 17 is located between 35% and 45% of length of keel 20, from the toe end 18. Further, roll contact 17 is preferably slightly convex.

Mid-foot portion 40 comprises dome 22. Dome 22 is integral with mid-foot portion 40 and keel 20 (e.g., dome 22 may be molded or cast as part of keel 20). In other embodiments (not illustrated), dome 22 may be a distinct and separate component that is coupled to keel 20.

Figure 3:
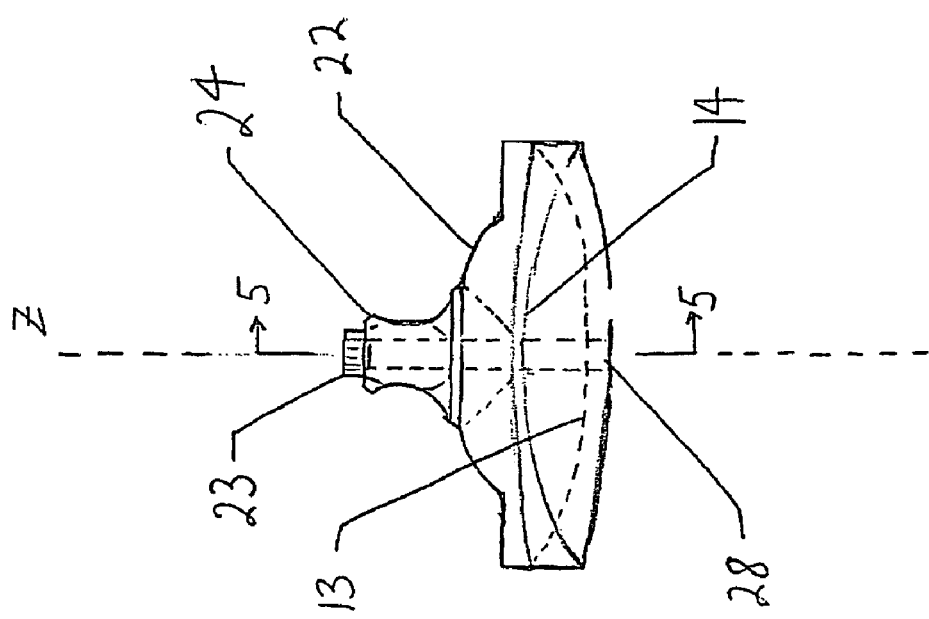
FIG. 3 is a rear view of the keel illustrated in FIG. 2.

Dome 22 has a centerline, represented by the z-axis, that is substantially perpendicular to longitudinal axis of keel 20 (best seen in FIGS. 2 and 3). It is to be understood that the longitudinal axis of keel 20 is an axis substantially parallel to the y-axis running the length of keel 20. Further, dome 22 is preferably substantially centered along the length and width of mid-foot portion 40. In different embodiments (not illustrated), dome 22 may be positioned off center relative to mid-foot portion 40. In addition, the length of mid-foot portion 40 is substantially the same as the length of dome 22. For example, mid-foot portion 40 may be defined by the location and length of dome 22, or vice versa. In alternative embodiments (not illustrated), mid-foot portion 40 and dome 22 may have different lengths.

In general, dome 22 may bear forces (e.g., weight) that are applied to keel 20 by an amputee wearing prosthetic foot 10. Dome 22 may have a relatively smooth surface capable of distributing applied forces. Without being limited by theory, by distributing forces, a relatively smooth surface may reduce or minimize stress concentrations which may otherwise result in premature damage or cracking of keel 20.

In addition, dome 22 preferably has a semi-spherical geometry. The semi-spherical geometry may permit for a variety of orientations of prosthetic foot 10 relative to an amputee when prosthetic foot 10 is coupled to the amputee. In particular, the semi-spherical geometry of dome 22 may permit the adjustment of keel 20 about the x-axis, the y-axis, and the z-axis, relative to the amputee. For example, when keel 20 is fitted to an amputee by an Otto Boch connector, the orientation of keel 20 may be adjusted about three axes by varying the position of the female socket of the Otto Boch connector relative to dome 22. Moreover, this feature of dome 22 allows subsequent adjustments of keel 20 about any of the three axes without the need to redesign keel 20.

Further, mid-foot portion 40 is contiguous with forefoot portion 30 and heel portion 50. There is a relatively seamless transition between forefoot portion 30 and mid-foot portion 40 and a relatively seamless transition between mid-foot portion 40 and heel portion 50. In different embodiments (not illustrated), the transition between mid-foot portion 40 and heel portion 50 and/or the transition between mid-foot portion 40 and forefoot portion 30 may be more abrupt (e.g., not smooth, rough, etc.).

FIG. 2 shows a cosmesis 15 (shown in phantom) that substantially surrounds keel 20 and provides the external appearance of prosthetic foot 10. In select embodiments, cosmesis 15 is constructed of foamed polyethylene and ethylene-vinyl acetate copolymer (EVA). Further, in certain embodiments, the inside of cosmesis is formed of expanded polyethylene and the outside is formed of expanded EVA, which provides superior abrasion resistance.

FIGS. 2 and 3 best illustrate borehole 28 and spindle 24 of mid-foot portion 40. Borehole 28 passes completely through mid-foot portion 40. However, in different embodiments (not illustrated), borehole 28 may pass through the top of dome 22 but not completely through mid-foot portion 40. Borehole 28 may be machined into keel 20 or may be molded or cast as part of keel 20.

Borehole 28 has a central axis, represented by the z-axis, that preferably substantially coincides with the centerline of dome 22. Further, in certain embodiments, the central axis of borehole 28 and the centerline of dome 22 are located between 65% and 85% of the length of keel 20 from toe end 18. Preferably, the central axis of borehole 28 and the centerline of dome 22 are located substantially between 70% and 80% of the length of keel 20 from toe end 18.

Still referring to FIGS. 2 and 3, borehole 28 accommodates spindle 24 and bolt 23. Spindle 24 is rotationally and translationally fixed relative to keel 20. In the embodiment shown, spindle 24 is bolted to keel 20 in mid-foot portion 40 by bolt 23. Bolt 23 engages mating threads in mid-foot portion 40. However, in general, spindle 24 may be secured to keel 20 by any suitable means including without limitation, adhesives, press fitting, pressure fitting, screws, bolts, or combinations thereof. Further, in other embodiments (not illustrated), spindle 24 may be integral with mid-foot portion 40. Spindle 24 is preferably provided at its upper end with a standard square prosthetic connector, such as an Otto Boch connector or the like.

In general, spindle 24 provides a means to couple keel 20, and prosthetic foot 10, to an amputee. For example, the portion of spindle 24 extending above dome 22 may be secured to a mating socket mounted on a liner worn by an amputee.

Still referring to FIGS. 2 and 3, heel portion 50 preferably includes an upward convcavity, or recess 13, and a heel end 14. Recess 13 (shown in phantom in FIGS. 2 and 3) is located on the topside of heel portion 50. By reducing the amount of material in heel portion 50, recess 13 may lighten keel 20. Further, by reducing the effective thickness of heel portion 50, recess 13 may permit greater flexibility, flexion, and bending of heel portion 50. In other embodiments (not illustrated), recess 13 may be provided in a different location on heel portion 50.

Figure 4:
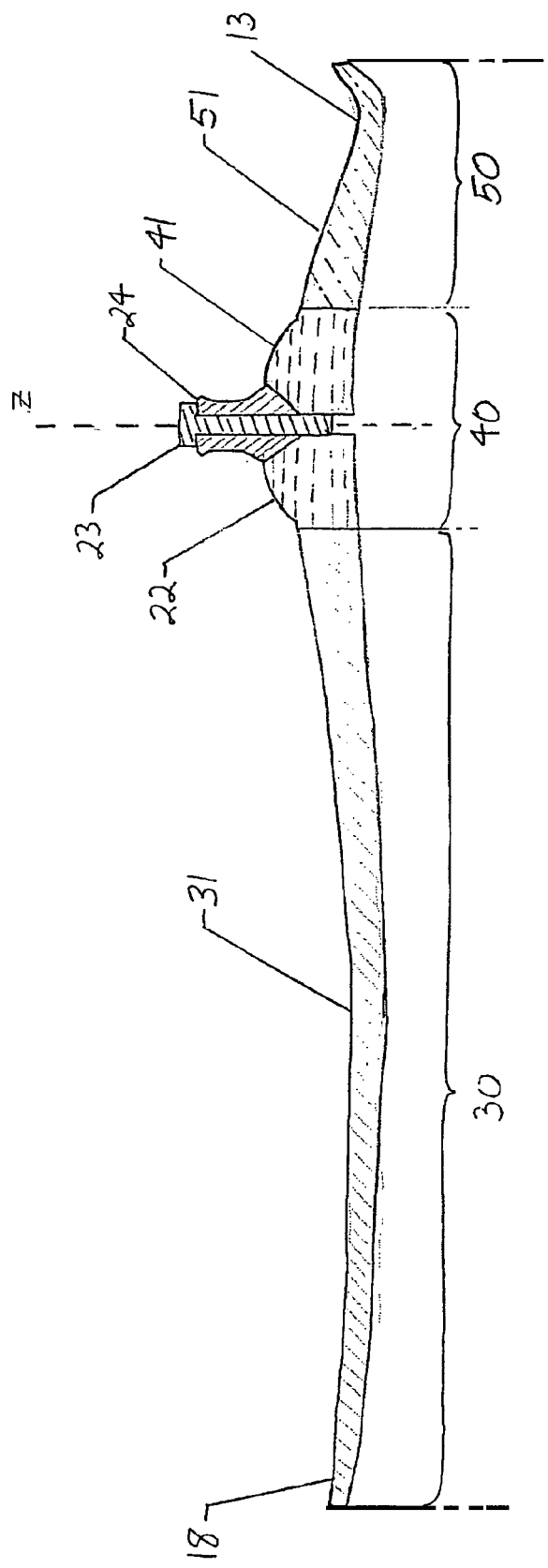
FIG. 4 is an enlarged schematic cross-section taken along lines 5-5 of FIG. 3.

FIG. 4 illustrates a cross-section of the embodiment of keel 20 illustrated in FIG. 2 taken along lines 5-5. Forefoot portion 30 is contiguous with mid-foot portion 40, and mid-foot portion 40 is contiguous with heel portion 50, however, each portion of keel 20 (e.g., forefoot portion 30, mid-foot portion 40, and heel portion 50) comprises a different material. Forefoot portion 30 comprises a first material 31, mid-foot portion 40 comprises a second material 41, and heel portion 50 comprises a third material 51. In alternative embodiments (not illustrated), different portions of keel 20 may comprise the same material.

First material 31 may comprise any suitable material(s) including without limitation metals and metal alloys (e.g., stainless steel, aluminum, titanium, etc.), non-metals (e.g., composite, polymer, elastomer, ceramic, etc.), or combinations thereof. Further, first material 31 may comprise more than one constituent material (e.g., laminate of different materials, composite, etc.).

Figure 5:
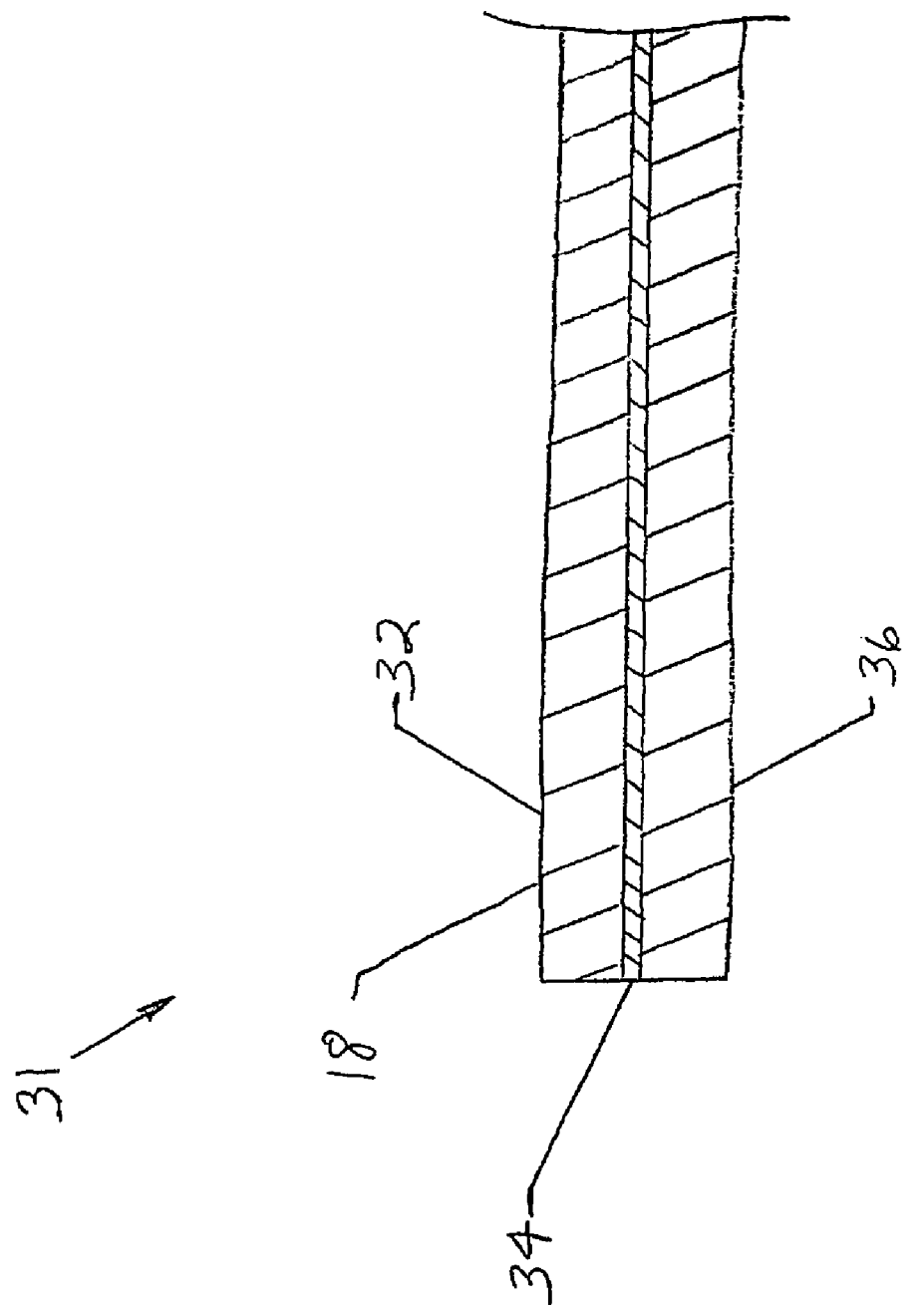
FIG. 5 is an enlarged schematic cross-section of an embodiment of the forefoot of the keel illustrated in FIG. 4.

FIG. 5 illustrates an embodiment of first material 31 shown in FIG. 4. In this embodiment, first material 31 comprises a top layer 32, a middle layer 34, and a bottom layer 36. In other embodiments, first material 31 may comprise one or more constituent material(s).

Middle layer 34 is positioned between top layer 32 and bottom layer 36. Middle layer 34 may be held in place by any suitable means including without limitation, adhesive, pressure, friction, screws, or combinations thereof. For example, middle layer 34 may be held in place by friction forces acting at the interface of middle layer 34 and top layer 32 and friction forces acting at the interface of middle layer 34 and bottom layer 36. The friction force may result from pressure exerted on middle layer 34 by top layer 32 and bottom layer 36. For instance, top layer 32 and bottom layer 36 may comprise relatively rigid materials that act as springs exerting force on middle layer 34 when middle layer 34 is inserted between top layer 32 and bottom layer 36 and tends to push apart top layer 32 and bottom layer 36. In select embodiments, middle layer 34 extends from toe end 18 to proximal the interface between forefoot portion 30 and mid-foot portion 40.

In select embodiments, top layer 32 and bottom layer 36 both comprise a relatively lightweight and rigid composite (e.g., glass fiber substrate and epoxy matrix composite, carbon fiber substrate and epoxy matrix composite, carbon and glass fiber substrate and epoxy matrix composite, etc.) and middle layer 34 comprises a more flexible elastomer or polymer (e.g., neoprene, polyethylene, cellulose acetate, polypropylene, etc.). In this configuration, top layer 32 and bottom layer 36 may provide a spring effect, while middle layer 34 may provide a cushion effect. The spring effect may provide a means to absorb, store, and release energy, thereby allowing keel 20 to return to a relaxed, unflexed position when applied forces are removed. Achievement of a spring effect without additional hardware (e.g., coil springs or other reciprocating means that absorb, store and release energy) may desirably reduce the weight of keel 20. Further, the use of composite materials in top layer 32 and bottom layer 36 may reduce the weight of keel 20 while providing some rigidity and strength.

Still further, this configuration may allow for some flexibility along the length of forefoot portion 30. The amount of flexion permitted by forefoot portion 30 is preferably at least 5°. For example, a carbon and glass fiber substrate and epoxy matrix composite top layer 32 and bottom layer 36 may permit 10° of flexion (dorsiflexion and/or planiflexion) of forefoot portion 30 relative to mid-foot portion 40 when keel 20 is fixed to an amputee. Depending on the overall length of forefoot portion 30, such flexion may permit toe end 18 to flex over half an inch relative to mid-foot portion 40. This flexion capability of forefoot portion 30 may be particularly desirable for Syme amputees who may rely on keel 20 to provide some of the flexion normally provided by an anatomical ankle. However, ultimately, the desired amount of flexion of forefoot portion 30 may be a function of numerous factors including without limitation, the personal preferences of the amputee, the activity level of the amputee, the weight of the amputee, whether amputee is geriatric, or combinations thereof.

As illustrated in FIGS. 2 and 4, the thickness of forefoot portion 30, and first material 31, vary along the length of forefoot portion 30. In particular, the thickness of forefoot portion 30 tapers from mid-foot portion 40 to toe end 18. The taper of forefoot portion 30 may be linear or non-linear. In different embodiments (not illustrated), forefoot portion 30 may be a uniform thickness. In general, the thickness of forefoot portion 30 and any taper of forefoot portion 30 may be a function of numerous factors including without limitation, the length of forefoot portion 30, the length of keel 20, the intended use of prosthetic foot 10 (e.g., geriatric amputee, athletic amputee, etc.), the amount of desired flexion in keel 20, the desired weight of prosthetic foot 10, the forces applied to keel 20, or combinations thereof.

Referring again to FIG. 4, mid-foot portion 40 comprises second material 41. In addition, dome 22, which is integral with mid-foot portion 40, comprises second material 41.

Second material 41 may comprise any suitable material(s) including without limitation metals and metal alloys (e.g., stainless steel, aluminum, titanium, etc.), non-metals (e.g., composite, polymer, elastomer, ceramic, etc.), or combinations thereof. Further, second material 41 may comprise more than one constituent material (e.g., laminate of different materials, composite, etc.). Still further, in other embodiments (not illustrated), first material 31 and second material 41 may be the same material.

In select embodiments, second material 41 is a relatively lightweight and rigid material capable of withstanding the repeated application of forces to dome 22 and spindle 24 that may result each time the amputee takes a step with prosthetic foot 10. In addition, second material 41 is preferably capable of providing a firm base for which spindle 24 may be adequately secured (e.g., allow spindle 24 to be firmly secured to mid-foot portion 40 by bolt 23). For instance, it is desirable to have spindle 24 firmly and securely attached to keel 20 so that prosthetic foot 10 does not accidentally breakaway or disconnect from the amputee when the amputee is walking on prosthetic foot 10. In certain embodiments, second material 41 comprises a relatively lightweight, relatively strong, and relatively rigid fiber composite (e.g., glass fiber substrate and epoxy matrix composite, carbon fiber substrate and epoxy matrix composite, carbon and glass fiber substrate and epoxy matrix composite, etc.). Preferably, second material 41 comprises a carbon and glass fiber substrate and epoxy matrix composite.

Moreover, for additional strength and rigidity, mid-foot portion 40 may be made thicker (e.g., mid-foot portion 40 may be the thickest portion of keel 20). However, it is to be understood that increasing the thickness of mid-foot portion 40 may undesirably increase the weight of keel 20 and prosthetic foot 10. In addition, increasing the thickness of the mid-foot portion 40, or any portion of keel 20, may reduce the overall flexibility of keel 20. In particular, when used with Syme amputees, it may be undesirable to reduce the overall flexibility of keel 20 since keel 20 may be intended to partially simulate the flexion normally provided by an anatomical ankle.

As discussed above, dome 22 is integral with mid-foot portion 40. This configuration eliminates the need to externally attach dome 22 to keel 20. For example, in some prosthetic feet, a metal plate including a dome may be bolted to the keel through holes provided at the four corners of the metal plate. Any additional holes provided in the keel to bolt a metal plate to keel may weaken the keel. Further, stress concentrations may develop in the keel near the ends of any attached rigid metal plate. In particular, the area of the keel near the ends of the attached rigid metal plate may be locations of flexion. The weakening of the keel by additional holes in conjunction with the development of stress concentrations in roughly the same region may increase the susceptibility of the keel to premature cracking, breaking, or damage. To overcome this potential problem, the keel may be made thicker in the particular areas susceptible to premature damage (e.g., locations where additional holes are provided, locations near the end of any attached rigid plate, etc.). However, thickening of the keel may reduce the flexibility of the keel and may increase the weight of keel 20. In particular, reductions in flexibility of the keel arising as a result of any thickening of the keel may be undesirable for Syme amputees who may rely on the keel to provide some flexion.

Thus, referring to FIGS. 2 and 3, keel 20 preferably includes a single borehole 28 in mid-foot portion 40. By restructuring the connection of spindle 24 to keel 20 in this manner, weakening of mid-foot portion 40 and keel 20 may be minimized. In different embodiments (not illustrated), keel 20 may include more than one borehole 28.

In addition, borehole 28 is located substantially along the centerline of dome 22, represented by z-axis (best seen in FIGS. 2 and 3). By locating borehole 28 along the centerline of dome 22, borehole 28 passes through the thickest and strongest region of mid-foot portion 40. Further, since there is only one borehole 28, thickening of mid-foot region 40 (provided by dome 22) need only be provided in the general area around borehole 28. In this manner, the strength of keel 20 is increased (e.g., weakening due to holes is decreased) while minimally impacting the flexibility of keel 20.

As discussed above, dome 22 results in a thickening of mid-foot region 40 and second material 41. In other embodiments (not illustrated), mid-foot portion 40 may have a uniform thickness. Further in other embodiments (not illustrated), dome 20 may take the form of different geometries, which may affect the thickness of mid-foot portion 40. In general, the thickness of mid-foot portion 40 and second material 41 will tend to be a function of numerous factors including without limitation, the length of mid-foot portion 40, the length of keel 20, the intended use of keel 20 and prosthetic foot 10 (e.g., geriatric amputee, athletic amputee, etc.), the amount of flexion desired in keel 20, the desired weight of keel 20 and prosthetic foot 10, the forces applied to keel 20, location of high stress regions, or combinations thereof.

Referring again to FIG. 4, spindle 24 is rigidly secured to mid-foot portion 40 by bolt 23 which engages borehole 28. Spindle 24 may comprise any suitable material, including without limitation a metal or metal alloy (e.g., stainless steel, aluminum, etc.), a non-metal (e.g., polymer, composite, ceramic, etc.), or combinations thereof. In select embodiments, spindle 24 comprises a lightweight strong material. Spindle 24 preferably comprises titanium or a titanium alloy.

Still referring to FIG. 4, heel portion 50 comprises third material 51. Third material 51 may comprise one or more constituent material(s). Further, in other embodiments (not illustrated), second material 41 and third material 51 may be the same material.

In select embodiments, third material 51 may be a relatively lightweight and strong material capable of withstanding repeated application of forces (e.g., forces applied at heel end 14, etc.). Although strength is desirable, for Syme amputees, it may also be desirable for heel portion 50 to provide some flexion in order to partially simulate the flexion normally provided by an anatomical ankle. Thus, in certain embodiments, third material 51 comprises a relatively strong and relatively flexible composite capable of repeated slight bending without breaking. In some embodiments, third material 51 comprises a glass fiber substrate and epoxy matrix composite. In other embodiments, third material 51 comprises a carbon fiber substrate and epoxy matrix composite. Preferably, third material 51 comprises a carbon and glass fiber substrate and urethane matrix composite. The urethane preferably has a durometer rating between 75 and 85. In this configuration, heel portion 50 may be relatively strong, lightweight, yet flexible.

The amount of flexion permitted by heel portion 50 is preferably at least 5°. For example, a carbon and glass fiber substrate and urethane matrix composite (e.g., third material 51) may permit 10° of flexion (dorsiflexion and/or planiflexion) of heel portion 50 relative to mid-foot portion 40 when keel 20 is fixed to an amputee. Depending on the overall length of heel portion 50, such flexion may permit heel end 18 to flex over half an inch relative to mid-foot portion 40. These features are particularly desirable for Syme amputees who have sustained an ankle disarticulation and therefore may rely on heel portion 50 to partially simulate the flexion normally provided by an anatomical ankle. However, ultimately, the desired amount of flexion of heel portion 50 may be a function of numerous factors including without limitation, the personal preferences of the amputee, the activity level of the amputee, the weight of the amputee, whether amputee is geriatric, or combinations thereof.

As discussed above, heel portion 50 comprises a recess 13 (best seen in FIGS. 2 and 3). The inclusion of recess 13 in heel portion 50 results in the tapering of heel portion 50 from mid-foot portion 40 to heel end 14. The tapering of heel portion 50 may further enhance the flexibility of heel portion 50. Further, the tapering of heel portion 50 may reduce the weight of keel 20.

Figure 6:
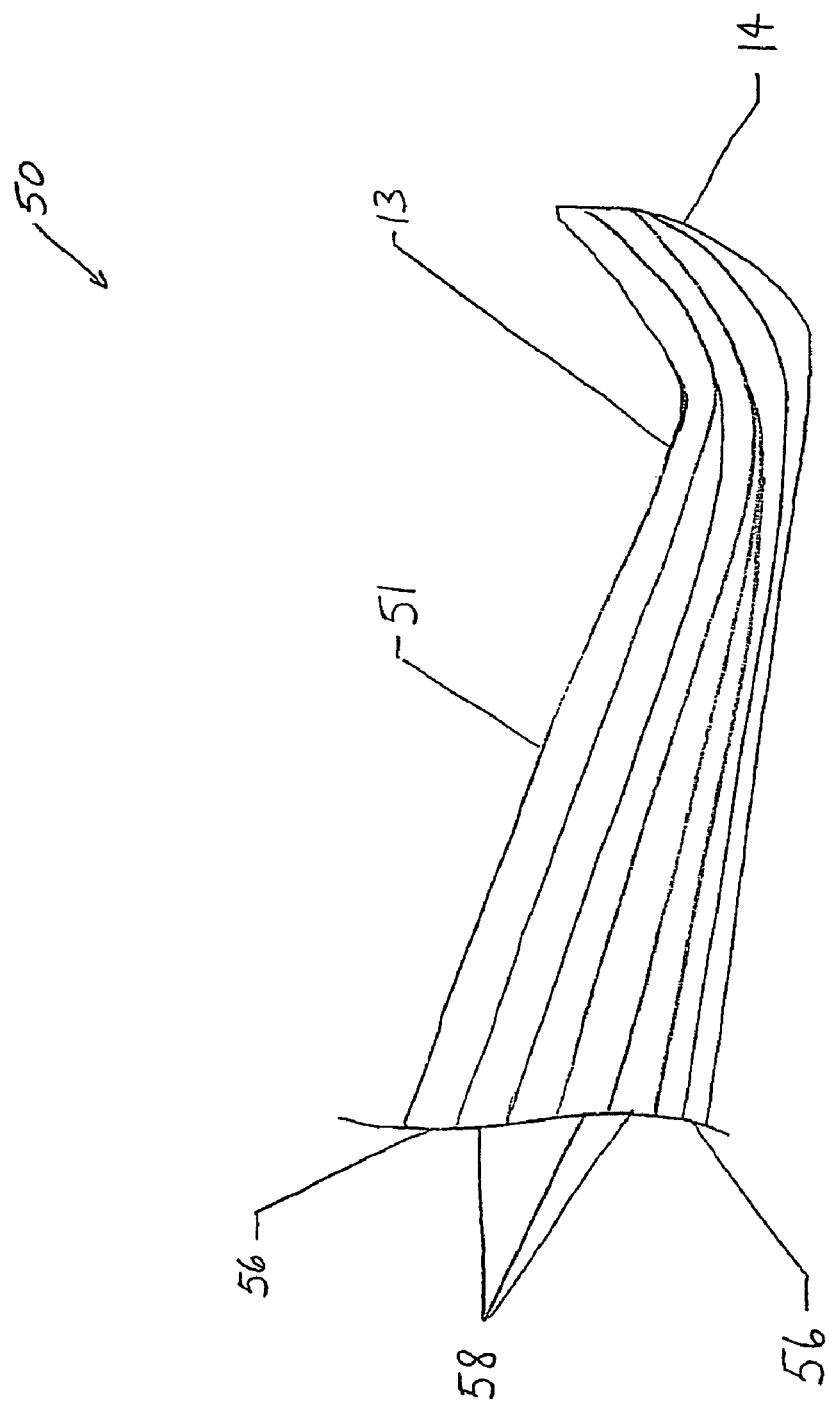
FIG. 6 is an enlarged schematic cross-section of an embodiment of the heel of the keel illustrated in FIG. 4.

FIG. 6 illustrates an embodiment of heel portion 50. In this embodiment, heel portion 50 and third material 51 comprise a fiber composite (e.g., glass fiber substrate and epoxy matrix composite, carbon fiber substrate and epoxy matrix composite, carbon and glass fiber substrate and epoxy matrix, etc.). Heel portion 50 is preferably formed by a plurality of short fibers 58 and a plurality of long fibers 56. Short fibers 58 extend from mid-foot portion 40 into heel portion 50, but do not fully extend to heel end 14. Long fibers 56 extend from mid-foot portion 40 to heel end 14, fully through heel portion 50. In this manner, by reducing the total number of fibers along the length of heel portion 50 from mid-foot portion 40 to heel end 14, the effective thickness of heel portion 50 is reduced, resulting in recess 13. In certain embodiments, long fibers 56 (e.g., fibers that extend from mid-foot portion 40 through heel end 14) represent 25% of the substrate fiber in heel portion 50 running along the longitudinal axis of keel 20, while short fibers 58 (e.g., fibers that do not extend completely to heel end 14) represent 75% of the substrate fibers in heel portion 50 running along the longitudinal axis of keel 20.

Keel 20 is preferably constructed of relatively lightweight and strong composite materials. As discussed above, each portion of keel 20 may comprise a different composite material. Preferably first material 31 (forefoot portion 30), second material 41 (mid-foot portion 40), and third material 51 (heel portion 50) each comprise a composite material that share a common substrate that extends through the forefoot, the mid-foot, and the heel. For example, first material 31 may comprise a carbon and glass fiber substrate and epoxy matrix composite and a neoprene middle layer 34, second material 41 may comprise a carbon and glass fiber substrate and epoxy matrix composite, and third material 51 may comprise a carbon and glass fiber substrate and urethane matrix composite. In this configuration, some carbon and glass fibers (substrate) may extend through first material 31, second material 41, and third material 51. This arrangement may result in a contiguous, unitary, and relatively strong keel 20, yet allow for distinct mechanical characteristics in each portion of keel 20. For example, forefoot 30 may provide a spring effect, cushion, and some flexion; mid-foot portion 40 may provide a rigid, relatively inflexible base; and heel portion 50 may provide a relatively strong, yet flexible material. By providing common fibers (substrate) throughout keel 20, but varying the matrix and/or additional layers within each portion of keel 20, each portion of keel 20 may be custom designed to provide characteristics desirable for particular types of amputees. In particular, embodiments of the present invention provide for a dynamic response prosthetic foot for Syme amputees designed to provide sufficient flexion to partially simulate the flexion normally provided by the anatomical ankle.

Several useful discussions of the context and usage of prosthetic feet are given in U.S. Pat. Nos. 5,482,513, 5,443, 527, 5,116,384, which are all hereby incorporated by reference herein in their entireties. For example, the construction of a suitable cosmesis, prosthetic leg attachment, and composition of various components can be derived from those disclosures.

In the manner described, embodiments of the present invention provide certain mechanical improvements over the prior art. Some embodiments of the present invention have the advantage of providing a relatively lightweight prosthetic foot keel capable of partially simulating the flexion normally provided by an anatomical ankle. In addition, embodiments of the present invention have the advantage of providing an integral semi-spherical dome 22 allowing for the adjustment of prosthetic foot 10 about three axes. Further, embodiments of the present invention have the advantage of providing a relatively rigid and secure mid-foot portion 40 for coupling prosthetic foot 10 to an amputee without unduly weakening or reducing the flexibility of the keel.

While preferred embodiments of this invention have been shown and described, modifications thereof can be made by one skilled in the art without departing from the scope or teaching of this invention. The embodiments described herein are exemplary only and are not limiting. Many variations and modifications of the system and apparatus are possible and are within the scope of the invention. For example, the relative dimensions of various parts, the materials from which the various parts are made, and other parameters can be varied, so long as the keel 20 device retains the advantages discussed herein. For instance, while the embodiments described above are preferably constructed of fiber composites because of its lightness, strength, flexibility and resiliency, it will be understood that other materials may be equally suitable. Accordingly, the scope of protection is not limited to the embodiments described herein, but is only limited by the claims that follow, the scope of which shall include all equivalents of the subject matter of the claims.

What is claimed is:

1. A keel for a prosthetic foot, comprising:
   a forefoot portion having a toe end;
   a mid-foot portion contiguous with the forefoot portion;
   a heel portion contiguous with the mid-foot portion;
   wherein the forefoot portion, the mid-foot portion, and the heel portion are monolithically formed;
   wherein the forefoot portion comprises a first material, the mid-foot portion comprises a second material, and the heel portion comprises a third material;
   wherein the first material comprises a first composite material including a substrate and a matrix, the second material comprises a second composite material including a substrate and a matrix, and the third material comprises a third composite material including a substrate and a matrix;
   wherein the substrate of the first material, the substrate of the second material, and the substrate of the third material share a plurality of common fibers that extend from the toe end to the heel end through the forefoot portion, the mid-foot portion, and the heel portion;
   wherein the second material and third material comprise different materials, and wherein the third material is more flexible than the second material;
   wherein the first material includes an upper layer, a lower layer, and an intermediate layer disposed between the upper layer and the lower layer;
   wherein the upper layer and the lower layer each extend from the mid-foot portion to the toe end, and the intermediate layer extends from proximal the mid-foot portion to the toe end;
   wherein the intermediate layer is more flexible than the upper layer and the lower layer;
   a semi-spherical dome extending from the mid-foot portion, wherein the semi-spherical dome and the mid-foot portion are monolithic; and
   a spindle coupled to the mid-foot portion and adapted to couple the keel to an amputee, wherein the spindle engages the semi-spherical dome.

2. The keel of claim 1, wherein the first composite material is a fiber substrate and epoxy matrix composite.

3. The keel of claim 2, wherein the second composite material is a fiber substrate and urethane matrix composite.

4. The keel of claim 1, wherein the first composite material comprises a first substrate and a first matrix, and the second composite comprises a second substrate and a second matrix, wherein the first substrate and second substrate are the same material, and the first matrix and the second matrix are different materials.

5. The keel of claim 1, wherein the keel is spherically adjustable about three orthogonal axes relative to an amputee when the keel is coupled to the amputee.

6. The keel of claim 1, wherein the semi-spherical dome has a centerline substantially perpendicular to the longitudinal axis of the keel.

7. The keel of claim 6, wherein the centerline is located between 70% and 80% of the length of the keel from the toe end.

* * * * *